(12) United States Patent
Filas et al.

(10) Patent No.: US 10,287,873 B2
(45) Date of Patent: May 14, 2019

(54) WIRELESSLY TRANSMITTING DATA REPRESENTING DOWNHOLE OPERATION

(71) Applicant: Schlumberger Technology Corporation, Sugar Land, TX (US)

(72) Inventors: James G. Filas, Missouri City, TX (US); Christian C. Spring, Houston, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 175 days.

(21) Appl. No.: 15/119,112

(22) PCT Filed: Feb. 25, 2015

(86) PCT No.: PCT/US2015/017525
§ 371 (c)(1),
(2) Date: Aug. 15, 2016

(87) PCT Pub. No.: WO2015/130785
PCT Pub. Date: Sep. 3, 2015

(65) Prior Publication Data
US 2017/0051602 A1 Feb. 23, 2017

Related U.S. Application Data

(60) Provisional application No. 61/944,332, filed on Feb. 25, 2014.

(51) Int. Cl.
*E21B 47/06* (2012.01)
*E21B 43/116* (2006.01)
(Continued)

(52) U.S. Cl.
CPC ............ *E21B 47/06* (2013.01); *E21B 43/116* (2013.01); *E21B 43/26* (2013.01); *E21B 47/12* (2013.01);
(Continued)

(58) Field of Classification Search
CPC ........ E21B 47/06; E21B 43/11; E21B 43/116; E21B 47/12; E21B 43/26; E21B 47/14; E21B 47/122; G01N 7/00
See application file for complete search history.

(56) References Cited

U.S. PATENT DOCUMENTS

2004/0089449 A1* 5/2004 Walton .................... E21B 21/00
166/297
2005/0242807 A1 11/2005 Freedman
(Continued)

FOREIGN PATENT DOCUMENTS

CN 1408984 4/2003
CN 1408984 A 4/2003
(Continued)

OTHER PUBLICATIONS

International Preliminary Report on patentability issued in the related PCT Application PCT/US2015/017525, dated Aug. 30, 2016 (10 pages).
(Continued)

*Primary Examiner* — Brad Harcourt
(74) *Attorney, Agent, or Firm* — Cameron R. Sneddon

(57) ABSTRACT

A system and method for transmitting data from within a wellbore to a surface location includes downhole tool that is nm into the wellbore. The downhole tool includes a sensor, a processor, and a transmitter. A pressure response in the wellbore is measured with the sensor. A function that
(Continued)

approximates the pressure response is determined. The function is transmitted to the surface location with the transmitter.

20 Claims, 6 Drawing Sheets

(51) Int. Cl.
    *E21B 47/14*     (2006.01)
    *E21B 43/26*     (2006.01)
    *G01N 7/00*     (2006.01)
    *E21B 47/12*     (2012.01)

(52) U.S. Cl.
    CPC ............... *E21B 47/14* (2013.01); *G01N 7/00* (2013.01); *E21B 47/122* (2013.01)

(56) References Cited

U.S. PATENT DOCUMENTS

| | | | |
|---|---|---|---|
| 2007/0198192 A1 | 8/2007 | Hsu et al. | |
| 2008/0128132 A1 | 6/2008 | Wilcox et al. | |
| 2011/0162849 A1 | 7/2011 | Soliman et al. | |
| 2012/0152542 A1 | 6/2012 | Le | |
| 2012/0155219 A1 | 6/2012 | Alteirac et al. | |
| 2013/0135114 A1 | 5/2013 | Ringer et al. | |
| 2017/0030186 A1* | 2/2017 | Rodgers | G01V 11/002 |

FOREIGN PATENT DOCUMENTS

| | | | |
|---|---|---|---|
| EP | 2664743 A1 | 11/2013 | |
| WO | WO2007056121 A1 | 5/2007 | |

OTHER PUBLICATIONS

Extended European Search Report issued in the related EP Application EP15755245.6, dated Nov. 21, 2017 (7 pages).

PCT/US2015/017525 International Search Report and Written Opinion, dated Jun. 25, 2015, 14 pgs.

Office Action issued in the related EP Application EP15755245.6, dated Nov. 22, 2018 (4 pages).

* cited by examiner

WIRELESSLY TRANSMITTING DATA REPRESENTING DOWNHOLE OPERATION

CROSS-REFERENCE TO RELATED APPLICATIONS

This application claims priority to U.S. Provisional Patent Application having Ser. No. 61/944,332, filed on Feb. 25, 2014, entitled "Wirelessly Transmitting Data Representing Downhole Operation," to James Filas et al., the entirety of which is incorporated by reference herein.

FIELD

Embodiments described herein generally relate to downhole tools. More particularly, such embodiments relate systems and methods for wirelessly transmitting data from a downhole tool to a surface location.

BACKGROUND INFORMATION

During perforating operations in a wellbore, the pressure response may be measured by one or more sensors immediately after the perforating guns have fired. The sensors are capable of recording pressure versus time at very high frequencies such that the pressure transient within a few milliseconds of the firing of the perforating guns is captured. For example, the sensors are capable of measuring at a rate of thousands or millions of pressure points per second. As a result, the sensors are oftentimes referred to as "fast gauges."

The measured pressure response data is stored in a non-volatile memory and may be downloaded or read when the perforating gun is retrieved at the surface after the perforating operation is complete. The measured pressure response data may then be used to determine the quality of the perforations, the amount of perforation tunnel cleanup achieved immediately after the perforating guns have fired, and the like. If the data indicates that remedial actions should take place, the drill string may be run back into the wellbore again to perform the remedial actions. Thus, as may be appreciated, it would be beneficial to be able to transmit the data to the surface while the drill string remains in the wellbore.

Data may be transmitted up through a wellbore wirelessly using acoustic or electromagnetic signals. However, the data rates associated with such signals are oftentimes less than 100 bits/second or even less than 10 bits/second. These low data rates are inadequate to transmit the measured pressure response data to the surface in a reasonable amount of time. Furthermore, to transmit the entire data set would use large amounts of energy, which would quickly deplete the limited energy stored in the batteries in the wellbore. Data may also be transmitted up through the wellbore using a physical line or cable, however deployment of such a cable is not normally performed during perforating operations due to the added time, cost, and logistical complexities. Wired drill pipe or tubing may also be used to transmit data over a physical line but such techniques are not normally used during perforating operations due to logical considerations and a lack of availability of such hardware.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

A method for transmitting data from within a wellbore to a surface location is disclosed. The method includes running a downhole tool into the wellbore. The downhole tool includes a sensor, a processor, and a transmitter. A pressure response in the wellbore is measured with the sensor. A function that approximates the pressure response is determined. The function is transmitted to the surface location with the transmitter.

In another embodiment, the method includes running a downhole tool into the wellbore. The downhole tool includes a perforating gun, a sensor, a processor, and a transmitter. The perforating gun is fired, thereby generating a pressure response. The pressure response is measured in the wellbore with the sensor. A measured pressure response curve is generated based at least partially upon the pressure response. A function that approximates the measured pressure response curve is determined. An approximate curve is generated based at least partially upon the function. The measured pressure response curve, the one or more functions, the approximate curve, or a combination thereof is transmitted wirelessly from the transmitter to the surface location.

A computing system is also disclosed. The computing system includes a processor and a memory system including a non-transitory computer-readable medium storing instructions that, when executed by the processor, causes the computing system to perform operations. The operations include generating a measured pressure response curve based at least partially upon a pressure response that is measured by a sensor in a wellbore. The pressure response is generated by firing a perforating gun in the wellbore. A function that approximates the measured pressure response curve is determined. An approximate curve is generated based at least partially upon the function.

BRIEF DESCRIPTION OF THE DRAWINGS

So that the recited features may be understood in detail, a more particular description, briefly summarized above, may be had by reference to one or more embodiments, some of which are illustrated in the appended drawings. It is to be noted, however, that the appended drawings are illustrative embodiments, and are, therefore, not to be considered to limit the scope of the application.

DETAILED DESCRIPTION

Figure 1:
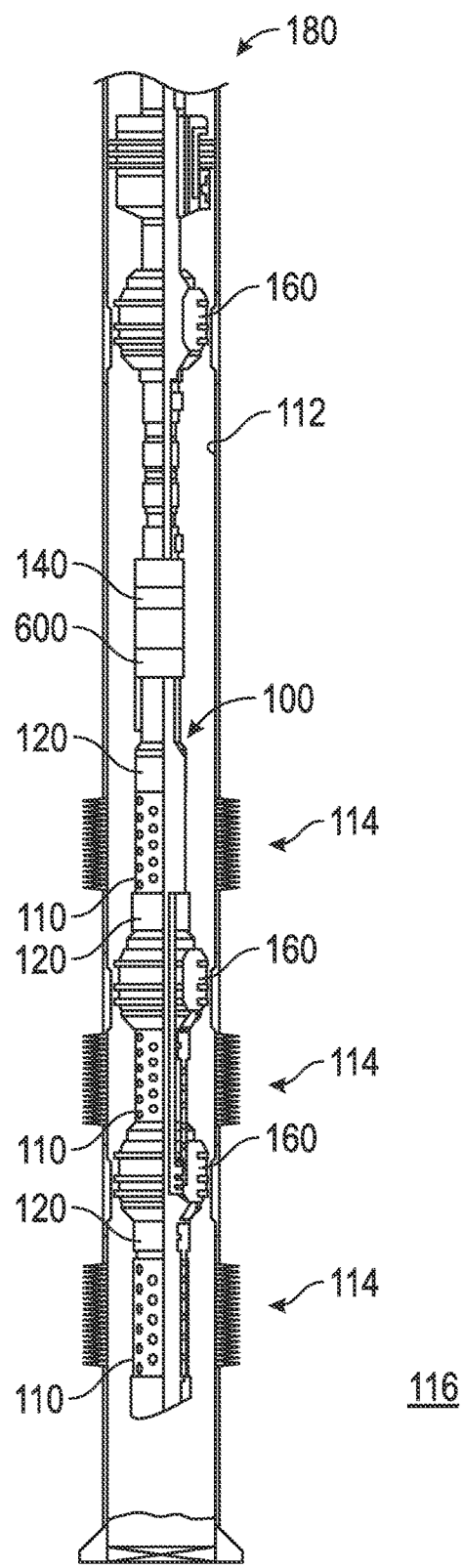
FIG. 1 depicts a partial cross-sectional view of an illustrative downhole tool in a wellbore, according to one or more embodiments disclosed.

FIG. 1 depicts a partial cross-sectional view of an illustrative downhole tool 100 in a wellbore 180, according to one or more embodiments disclosed. The downhole tool 100 may include one or more perforating guns (three are shown: 110). The perforating guns 110 may be configured to fire a plurality of charges to perforate (i.e., create openings in) a liner, casing, or other tubular member 112 positioned radially-outward therefrom. In FIG. 1, the perforations are shown at 114. This may create a plurality of flowpaths between the subterranean reservoir 116 and the interior of the tubular member 112.

The downhole tool 100 may also include one or more sensors (three are shown: 120). The sensors 120 may be axially-offset from one another, circumferentially-offset from one another, or both with respect to a central longitudinal axis through the downhole tool 100. As shown, each perforating gun 110 may have at least one sensor 120 coupled thereto or positioned proximate thereto (e.g., positioned above or below). The sensors 120 are configured to measure pressure over a period of time. For example, the sensors 120 may be "fast gauges" that are configured to take a plurality of pressure measurements over a predetermined period of time during the firing of the perforating guns 110 or shortly thereafter. The number of pressure measurements may range from about 10 to about 100, about 100 to about 1,000, about 1,000 to about 10,000, about 10,000 to about 100,000, or about 100,000 to about 1,000,000. The time period may be from about 10 μs to about 100 μs, about 100 μs to about 1 ms, about 1 ms to about 10 ms, about 10 ms to about 100 ms, or about 100 ms to about 1 s.

The downhole tool 100 may also include one or more computing systems (one is shown: 600) that is in communication with the sensors 120. The computing system 600 may be configured to receive the measured pressure response data from the sensors 120, which may be raw data including a plurality of pressure points and their corresponding times. The computer system 600 may then convert the measured pressure response data into one or more measured pressure response curves that show pressure versus time, as described in further detail below with respect to FIGS. 2-4.

The computer system 600 may determine one or more functions that most closely approximate the measured pressure response curve. Illustrative functions may be or include linear, polynomial, exponential, sinusoidal, logarithmic, combinations thereof, and the like. The functions may be assembled to form an approximate curve that closely resembles the corresponding measured pressure response curve.

The downhole tool 100 may also include one or more transmitters (one is shown: 140) that is in communication with the computing system 600. The transmitter 140 may be configured to transmit the functions up to a surface location where they may be read and analyzed by an operator. The functions may be transmitted wirelessly using acoustic or electromagnetic signals. In another embodiment, the functions may be transmitted through a cable.

The functions may be captured using less data (e.g., bits) than the measured pressure response data from which they are derived. For example, the functions may be captured using less than about 10%, less than about 8%, less than about 6%, less than about 4%, less than about 2%, or less than about 1% of the measured pressure response data from which they are derived. As will be appreciated, this may allow the information to be transmitted to the surface location in a shorter period of time. Other methods of data compression may be used alone, or in combination with, the determination of functions and corresponding approximate curves to obtain further transmission efficiencies. For example, compression methods such as Lempel-Ziv (LZ) or other methods where token entries are substituted for repeated strings of data may be used to improve efficiency when transmitting data to the surface representing the pressure response. In another example, the compression method may include the Ramer-Douglas-Peucker algorithm.

The wireless signal from the transmitter 140 may attenuate over the distance travelled. In at least one embodiment, the distance between the transmitter 140 and the surface location may be so great that the signal may not be received at the surface. Thus, the downhole tool 100 may also include one or more repeaters. In another embodiment, the repeater may be positioned in the wellbore 180 but not coupled to the downhole tool 100. For example, the repeater may be coupled to a casing, a drill string, a coiled tubing, a slickline, or other tubular member in the wellbore 180. The repeater may be configured to receive the wireless signal from the transmitter 140, and to amplify and retransmit the signal, enabling the signal to be received at the surface location.

The downhole tool 100 may also include one or more packers (three are shown: 160). Each of the packers 160 may be configured to expand radially-outward to contact the tubular 112 to separate the annulus between the downhole tool 100 and the tubular 112 into two (e.g., upper and lower) portions.

Figure 2:
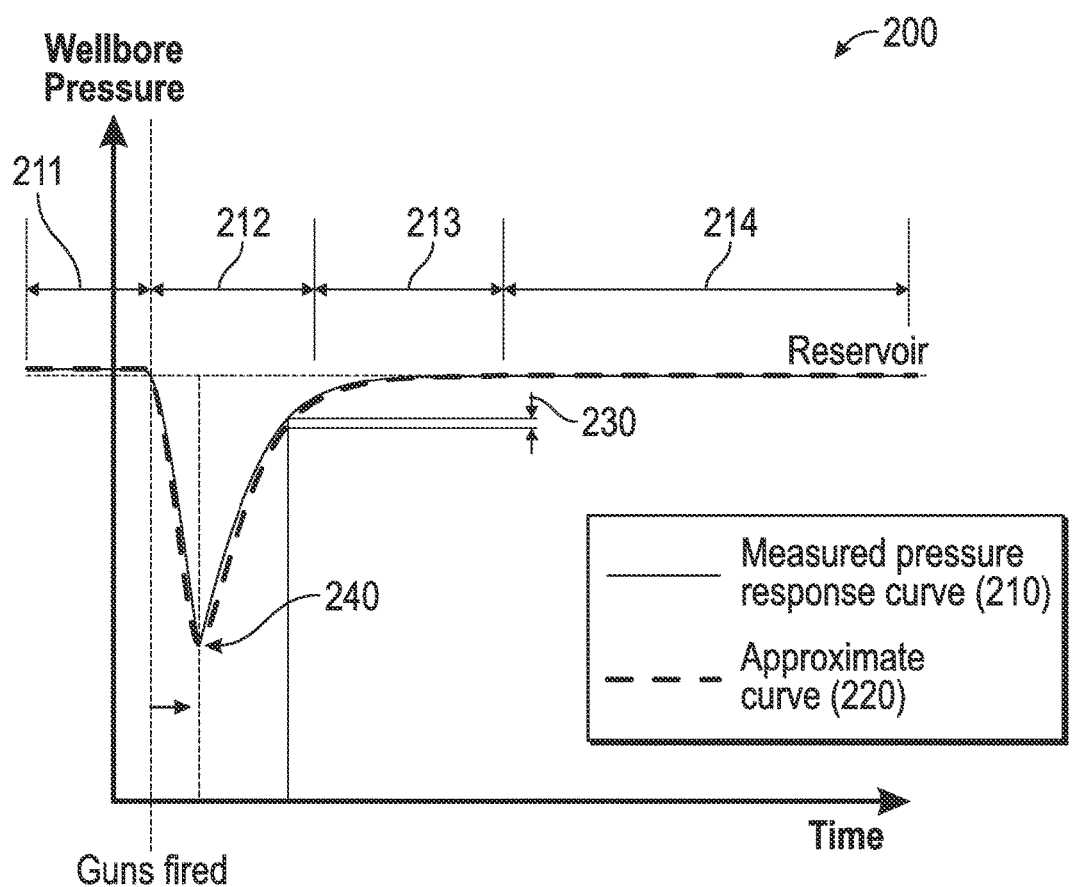
FIG. 2 depicts a graph of an illustrative measured pressure response curve (obtained using a perforating technique designed to achieve a dynamic underbalance) and a corresponding approximate curve that is represented by a plurality of polynomial functions, according to one or more embodiments disclosed.

FIG. 2 depicts a graph 200 of an illustrative measured pressure response curve 210 (obtained using a method to induce a dynamic pressure underbalance immediately after the firing of the perforating guns) and a corresponding approximate curve 220 that is represented by a plurality of polynomial functions, according to one or more embodiments disclosed. The dynamic underbalance minimizes or eliminates perforation damage by optimizing the transient cleanup of the wellbore 180, just after the creation of the perforation cavities. This approach relies on the immediate underbalance to improve perforation cleanup rather than allowing an overbalanced condition to cause the initial fluids in the wellbore, such as drilling muds or completion brines, to immediately enter the perforated formation and cause damage. Generating cleaner perforations results in a more efficient communication between the reservoir 116 and the wellbore 180 for improved well performance.

Referring back to the graph 200, the measured pressure response curve 210 may be separated into a plurality of segments (four are shown: 211-214). The computer system 600 may determine a function (including the corresponding coefficients) that most closely approximates each segment 211-214 of the measured pressure response curve 210. In at least one embodiment, the computer system 600 may include a library of functions stored in a memory, and the computer system 600 may compare each of the segments 211-214 of the measured pressure response curve 210 with the functions in the library to determine and select the best-fit functions from the library. The comparison may include performing one or more regression algorithms such as the methods of ordinary or total least squares, maximum likelihood, a combination thereof, and the like.

For example, as shown, the computer system 600 may select a linear function to represent the first segment 211, a third degree polynomial function to represent the second segment 212, a second degree polynomial to represent the third segment 213, and a linear function to represent the fourth segment 214. The functions (e.g., when assembled or combined) may form the approximate curve 220 on the graph 200 that closely resembles the measured pressure response curve 210.

A maximum error 230 between the measured pressure response curve 210 and the approximate curve 220 may be determined. Although a single maximum error 230 is shown, in other embodiments, a maximum error 230 may be determined for each of the segments 211-214. The maximum error 230 is the greatest distance (measured parallel to the Y axis) between the measured pressure response curve 210 and the approximate curve 220.

Figure 3:
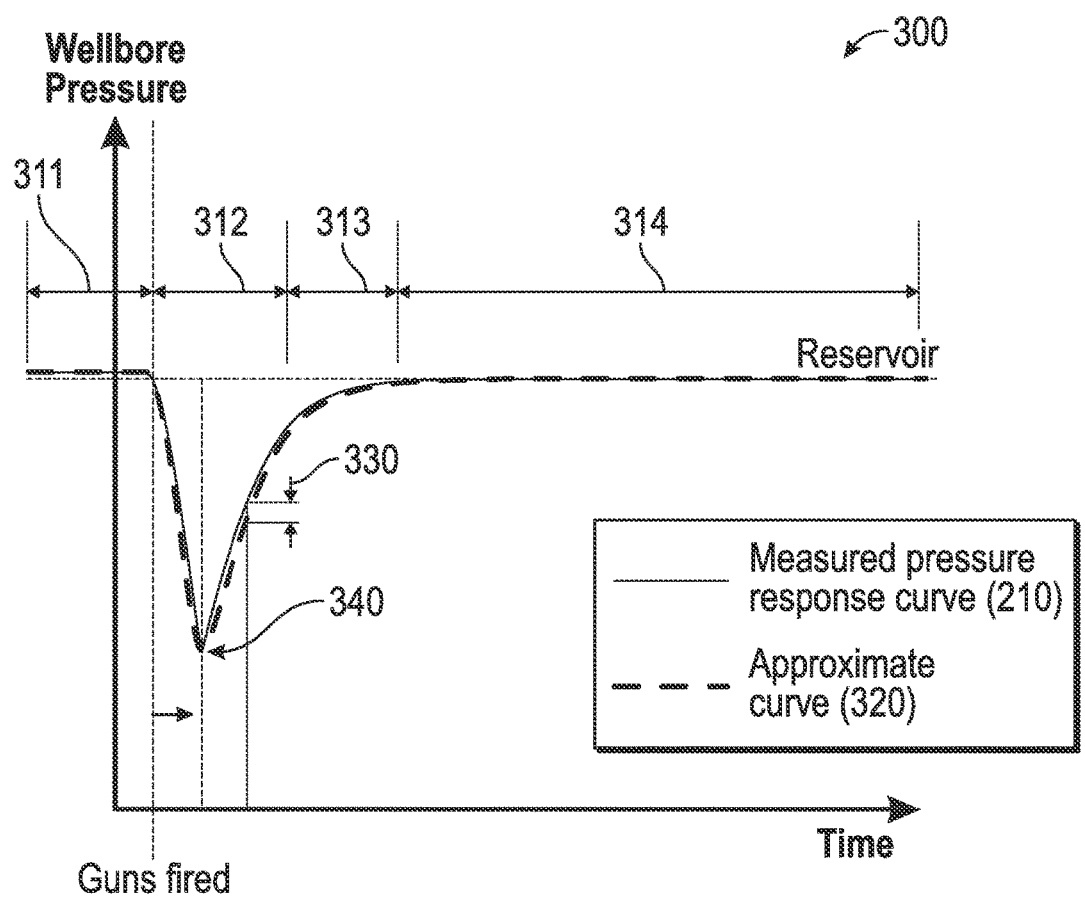
FIG. 3 depicts a graph of the measured pressure response curve from FIG. 2 and a corresponding approximate curve that is represented by a plurality of linear functions, according to one or more embodiments disclosed.

FIG. 3 depicts a graph 300 of the measured pressure response curve 210 from FIG. 2 and a corresponding approximate curve 320 represented by a plurality of linear functions, according to one or more embodiments disclosed. The measured pressure response curve 210 may be separated into a plurality of segments (four are shown: 311-314). In this embodiment, the computer system 600 may select linear segments to represent each of the segments 311-314.

As will be appreciated, the segments 311-314 in FIG. 3 differ from the segments 211-214 in FIG. 2 to adjust for the type of functions selected. For example, the portion of the measured pressure response curve 210 including the maximum dynamic underbalance 240 is shown as a substantially "V-shaped" portion of the curve 210. The majority of this V-shaped portion of the measured pressure response curve 210 may be represented by a single polynomial function, as described above with respect to FIG. 2. Accordingly, a single segment 212 is selected for the (V-shaped) portion of the measured pressure response curve 210 represented by this polynomial function.

In contrast, in the embodiment of FIG. 3, the majority of the V-shaped portion of the measured pressure response curve 210 may be represented by two linear functions. Accordingly, a two segments 312, 313 are selected for the (V-shaped) portion of the measured pressure response curve 210 represented by the two linear functions. Thus, as will be appreciated, the number of segments and the positioning of the segments may at least partially depend on the type of functions selected.

A maximum error 330 between the measured pressure response curve 210 and the approximate curve 320 may again be determined. The maximum error 330 shown in FIG. 3 is greater than the maximum error 230 shown in FIG. 2. This means that the polynomial function(s) selected in the embodiment of FIG. 2 are a better fit to match the measured pressure response curve 210 than the linear functions selected in the embodiment of FIG. 3. As a result, the approximate curve 220 in FIG. 2 more closely resembles the measured pressure response curve 210 than the approximate curve 320 in FIG. 3. Thus, while the computer system 600 may consider many functions and curves, including those shown in FIGS. 2 and 3, in this example, the computer system 600 may select the functions that form the approximate curve 220 in FIG. 2 instead of the functions that form the approximate curve 320 in FIG. 3.

Figure 4:
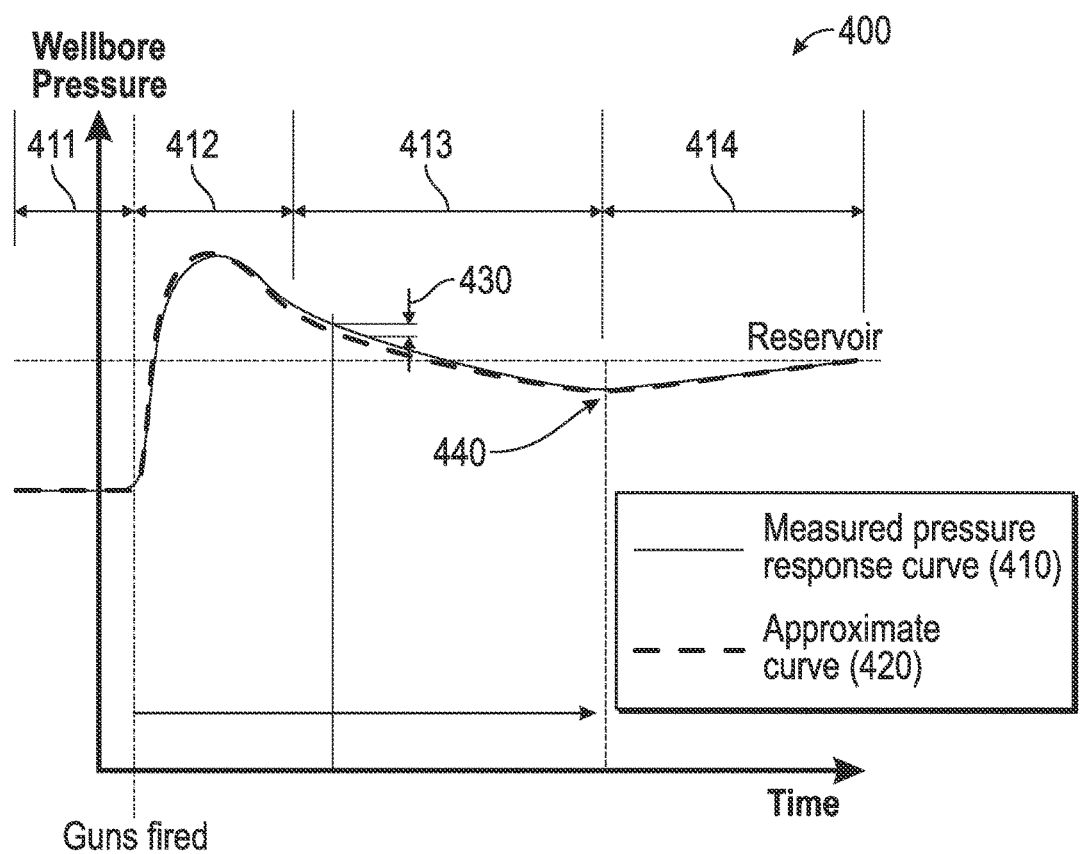
FIG. 4 depicts a graph of an illustrative measured pressure response curve (obtained using a perforating technique resulting in a substantial dynamic overbalance) and a corresponding approximate curve that is represented by a plurality of polynomial functions, according to one or more embodiments disclosed.

FIG. 4 depicts a graph 400 of an illustrative measured pressure response curve 410 (obtained using a perforating method which does not purposely induce a dynamic underbalance) and a corresponding approximate curve 420 represented by a plurality of polynomial functions, according to one or more embodiments disclosed. The measured pressure response curve 410 obtained using a non-PURE method may appear different than the measured pressure response curve 210 obtained using method which purposely generates a dynamic underbalance (as shown in FIGS. 2 and 3). For example, the maximum dynamic underbalance 440 in the measured pressure response curve 410 in FIG. 4 may be less than the maximum dynamic underbalance 240 in the measured pressure response curve 210 in FIGS. 2 and 3. However, the approach for determining the functions and forming the approximate curve 420 may be similar.

The measured pressure response curve 410 may be separated into a plurality of segments (four are shown: 411-414). The computer system 600 may determine a function (including the corresponding coefficients) that most closely approximates each segment 411-414 of the measured pressure response curve 410. In the embodiment shown in FIG. 4, the computer system 600 may select a linear function to represent the first segment 411, a third degree polynomial to represent the second segment 412, a second degree polynomial to represent the third segment 413, and third degree polynomial to represent the fourth segment 414.

A maximum error 430 between the measured pressure response curve 410 and the approximate curve 420 may be determined. Although a single maximum error 430 is shown, in other embodiments, a maximum error 430 may be determined for each of the segments 411-414.

Figure 5:
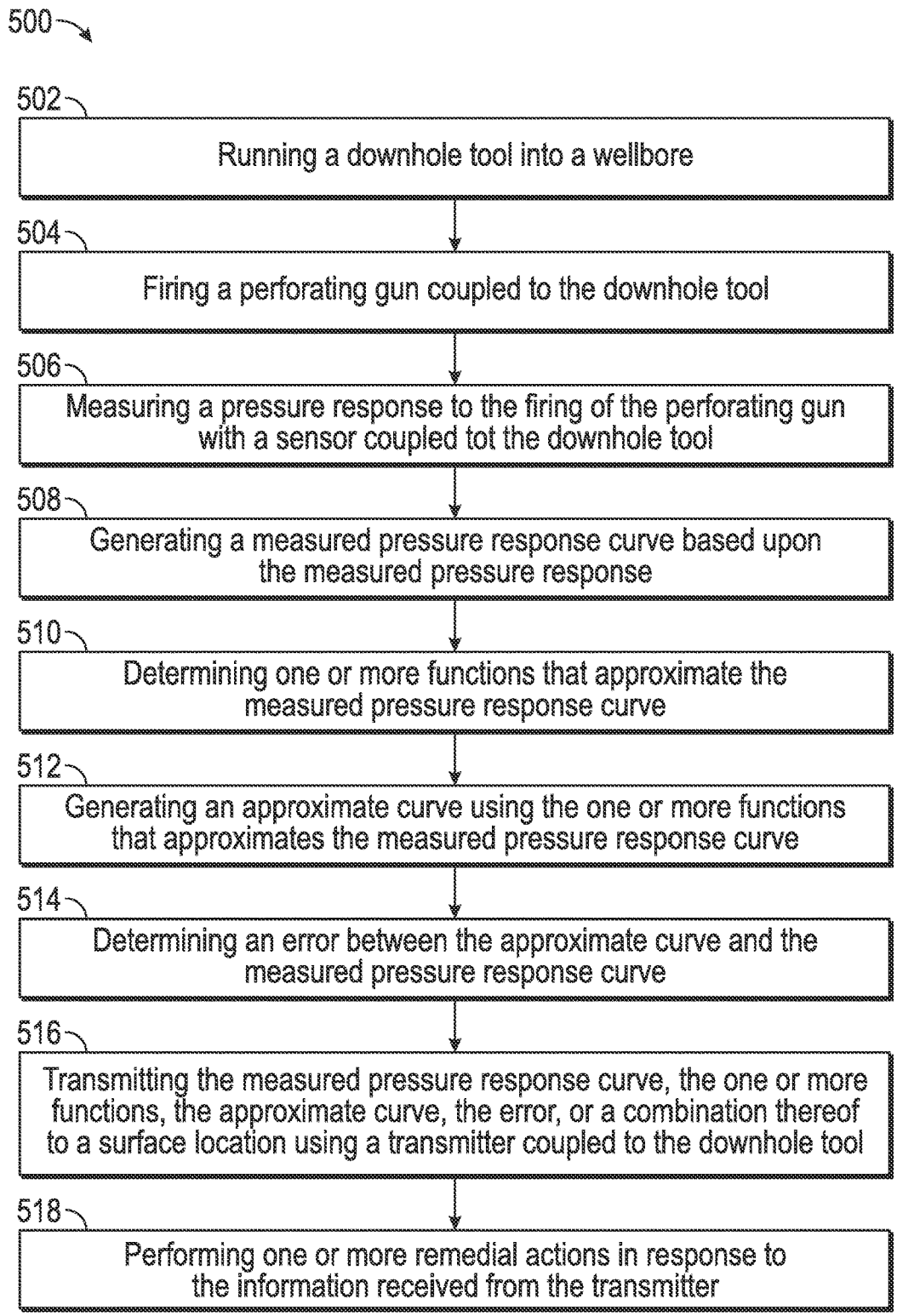
FIG. 5 depicts a flowchart of a method for transmitting data from within a wellbore to a surface location, according to one or more embodiments disclosed.

FIG. 5 depicts a flowchart of a method 500 for transmitting data from within a wellbore 180 to a surface location, according to one or more embodiments disclosed. The method 500 is described with respect to the downhole tool 100 described above; however, as will be appreciated, the at least a portion of the method 500 may be performed with other downhole tools.

The method 500 may include running the downhole tool 100 into the wellbore 180, as at 502. The downhole tool 100 may be or include the perforating gun 110, the computer system 600, and the transmitter 140. The perforating gun 110 may be fired, as at 504, to create a plurality of perforations in the tubular 112 (e.g., a liner or casing) positioned radially-outward from the perforating gun 110.

The sensor(s) 120 may measure a pressure response to the firing of the perforating gun 110, as at 506. In at least one embodiment, the computer system 600 may generate a measured pressure response curve 210, 410 based at least partially upon the measured pressure response (raw data), as at 508. The computer system 600 may determine one or more functions (and corresponding coefficients) that most closely approximate the measured pressure response (e.g., the raw data or the corresponding measured pressure response curve 210, 410), as at 510. In at least one embodiment, the computer system 600 may generate an approximate curve 220, 320, 420 using the functions that closely resembles the corresponding measured pressure response curve 210, 410, as at 512. The computer system 600 may then determine an error 230, 330, 430 between pressure response raw data and the one or more corresponding functions or between the measured pressure response curve 210, 410 and the corresponding approximate curve 220, 320, 420, as at 514.

The measured pressure response curve 210, 410, the one or more functions, the corresponding coefficients, the approximate curve 220, 320, 410, the error 230, 330, 430, or a combination thereof may then be transmitted from the downhole tool 100 to the surface location with the transmitter 140, as at 516. In response to information received by the transmitter 140, the operator may perform one or more remedial actions in the wellbore 180, as at 518. The remedial actions may occur without removing the downhole tool 100 from the wellbore 180. For example, if the information indicates that the perforation tunnels were not cleaned out to a predetermined degree during the perforation process, then the operator may perform the one or more remedial actions in the wellbore 180. The remedial actions may include pumping a fluid into the wellbore (e.g., through the drill string, coiled tubing, etc.). The fluid may be used to hydraulically fracture the formation. In another embodiment, the fluid may be an acid that is configured to remove near-well formation damage and other damaging substances to enhance production.

Figure 6:
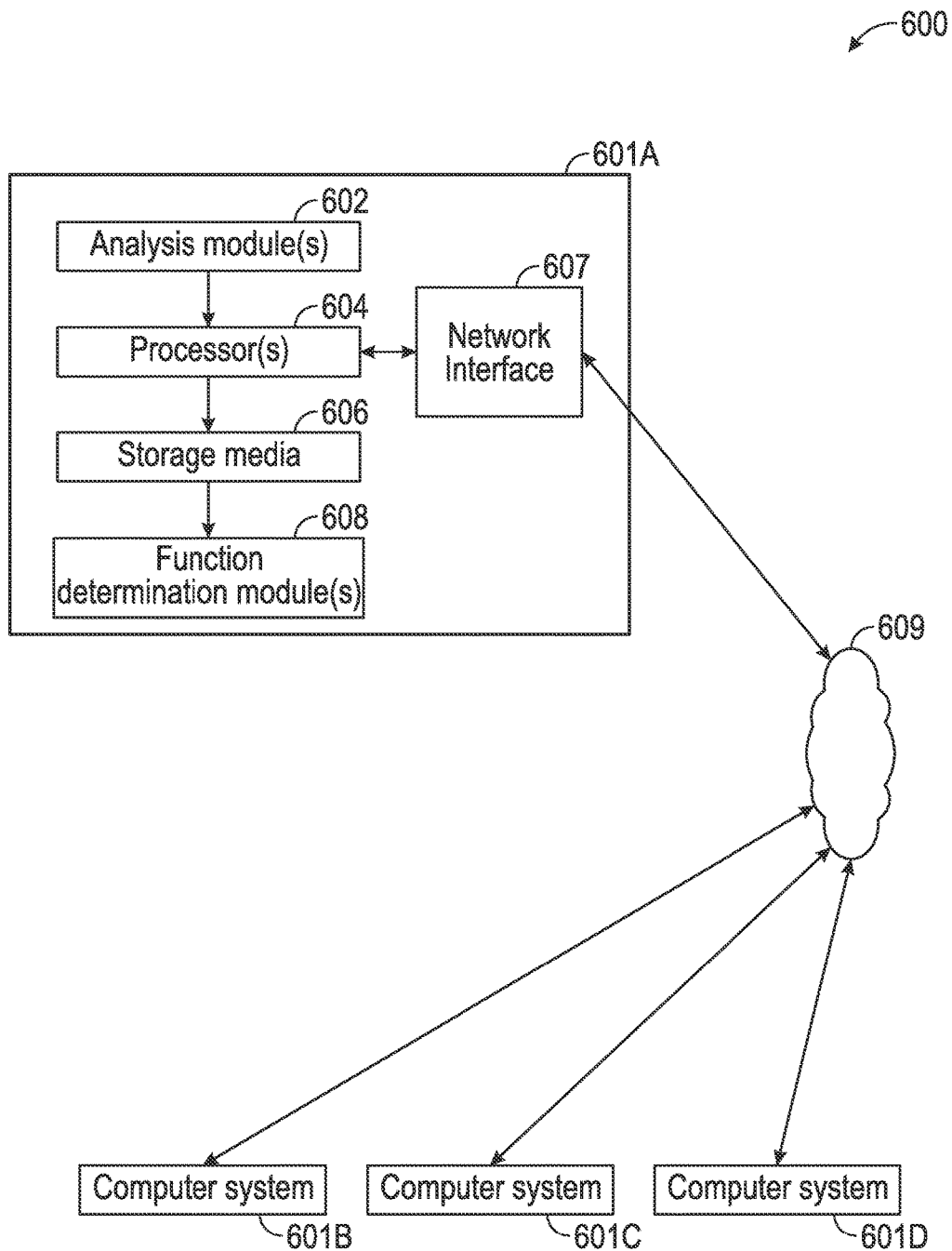
FIG. 6 illustrates a schematic view of a computing system for performing one or more of the methods disclosed herein, according to one or more embodiments disclosed.

FIG. 6 illustrates a schematic view of the computing system 600 for performing one or more of the methods disclosed herein, according to one or more embodiments disclosed. The computing system 600 may include a computer or computer system 601A, which may be an individual computer system 601A or an arrangement of distributed computer systems. The computer system 601A includes one or more analysis modules 602 that are configured to perform various tasks according to some embodiments, such as one or more methods disclosed herein. To perform these various tasks, the analysis module 602 executes independently, or in coordination with, one or more processors 604, which is (or are) connected to one or more storage media 606A. The processor(s) 604 is (or are) also connected to a network interface 607 to allow the computer system 601A to communicate over a data network 609 with one or more additional computer systems and/or computing systems, such as 601B, 601C, and/or 601D.

A processor can include a microprocessor, microcontroller, processor module or subsystem, programmable integrated circuit, programmable gate array, or another control or computing device. The storage media 606 can be implemented as one or more computer-readable or machine-readable storage media. Note that while in the example embodiment of FIG. 6 storage media 606 is depicted as within computer system 601A, in some embodiments, storage media 606 may be distributed within and/or across multiple internal and/or external enclosures of computing system 601 and/or additional computing systems. Storage media 606 may include one or more different forms of memory including semiconductor memory devices such as dynamic or static random access memories (DRAMs or SRAMs), erasable and programmable read-only memories (EPROMs), electrically erasable and programmable read-only memories (EEPROMs) and flash memories, or other types of optical storage, or other types of storage devices. Note that the instructions discussed above can be provided on one computer-readable or machine-readable storage medium, or in other embodiments, can be provided on multiple computer-readable or machine-readable storage media distributed in a large system having possibly plural nodes. Such computer-readable or machine-readable storage medium or media is (are) considered to be part of an article (or article of manufacture). An article or article of manufacture can refer to any manufactured single component or multiple components. The storage medium or media can be located either in the machine running the machine-readable instructions, or located at a remote site from which machine-readable instructions can be downloaded over a network for execution.

In some embodiments, computing system 600 contains a function determination module 608 configured to determine the one or more functions that most closely approximate the measured pressure response curve 210, 410 (see FIGS. 2-4).

The function determination module 608 may include a library, as discussed above. It should be appreciated that computing system 600 is one example of a computing system, and that computing system 600 may have more or fewer components than shown, may combine additional components not depicted in the example embodiment of FIG. 6, and/or computing system 600 may have a different configuration or arrangement of the components depicted in FIG. 6. The various components shown in FIG. 6 may be implemented in hardware, software, or a combination of both hardware and software, including one or more signal processing and/or application specific integrated circuits.

Further, aspects of the processing methods described herein may be implemented by running one or more functional modules in information processing apparatus such as general purpose processors or application specific chips, such as ASICs, FPGAs, PLDs, or other appropriate devices.

The determination of functions may be refined in an iterative fashion; this concept is applicable to the methods as discussed herein. This can include use of feedback loops executed on an algorithmic basis, such as at a computing device (e.g., computing system 600), and/or through manual control by a user who may make determinations regarding whether a given step, action, template, model, or set of functions has become sufficiently accurate for the measured pressure response curve under consideration.

As used herein, the terms "inner" and "outer"; "up" and "down"; "upper" and "lower"; "upward" and "downward"; "above" and "below"; "inward" and "outward"; and other like terms as used herein refer to relative positions to one another and are not intended to denote a particular direction or spatial orientation. The terms "couple," "coupled," "connect," "connection," "connected," "in connection with," and "connecting" refer to "in direct connection with" or "in connection with via one or more intermediate elements or members."

Although the preceding description has been described herein with reference to particular means, materials, and embodiments, it is not intended to be limited to the particulars disclosed herein; rather, it extends to all functionally equivalent structures, methods, and uses, such as are contemplated within the scope of the appended claims. While the foregoing is directed to embodiments of the present invention, other and further embodiments of the invention may be devised without departing from the basic scope thereof.

What is claimed is:

1. A method for transmitting data from within a wellbore to a surface location, comprising:
   running a downhole tool into the wellbore, wherein the downhole tool comprises a sensor, a processor, and a transmitter;
   measuring a pressure response in the wellbore with the sensor;
   determining, using said processor, one or more functions that approximate the pressure response; and
   transmitting the one or more functions to the surface location with the transmitter.

2. The method of claim 1, further comprising firing a perforating gun of the downhole tool to generate the pressure response.

3. The method of claim 2, further comprising performing one or more remedial actions in the wellbore when the one or more functions received at the surface location indicate that one or more tunnels generated by the firing of the perforating gun are not cleaned out to a predetermined degree.

4. The method of claim 3, wherein the remedial actions are selected from the group consisting of hydraulic fracturing and acidizing.

5. The method of claim 1, wherein the one or more functions are selected from the group consisting of a linear function, a polynomial function, an exponential function, a sinusoidal function, a logarithmic function, and a combination thereof.

6. The method of claim 1, further comprising determining, using the processor, an error between the pressure response and the one or more functions.

7. The method of claim 1, further comprising generating, using the processor, a measured pressure response curve based at least partially upon the pressure response.

8. The method of claim 7, wherein the one or more functions approximate the measured pressure response curve.

9. The method of claim 8, further comprising generating, using the processor, an approximate curve based at least partially upon the one or more functions.

10. The method of claim 9, further comprising determining, using the processor, an error between the measured pressure response curve and the approximate curve.

11. A method for transmitting data from within a wellbore to a surface location, comprising:
running a downhole tool into the wellbore, wherein the downhole tool comprises a perforating gun, a sensor, a processor, and a transmitter;
firing the perforating gun, thereby generating a pressure response;
measuring the pressure response in the wellbore with the sensor;
generating, using the processor, a measured pressure response curve based at least partially upon the pressure response;
determining, using the processor, one or more functions that approximate the measured pressure response curve;
generating, using the processor, an approximate curve based at least partially upon the one or more functions; and,
wirelessly transmitting the measured pressure response curve, the one or more functions, the approximate curve, or a combination thereof from the transmitter to the surface location.

12. The method of claim 11, further comprising performing one or more remedial actions in the wellbore when the one or more functions received at the surface location indicate that one or more tunnels generated by the firing of the perforating gun are not cleaned out to a predetermined degree.

13. The method of claim 12, wherein the remedial actions are selected from the group consisting of hydraulic fracturing and acidizing.

14. The method of claim 13, wherein the remedial actions occur without removing the downhole tool from the wellbore.

15. The method of claim 14, determining, using the processor, an error between the measured pressure response curve and the approximate curve.

16. A downhole tool comprising:
a perforating gun; and,
a computing system comprising:
one or more processors;
a transmitter; and
a memory system comprising one or more non-transitory computer-readable media storing instructions that, when executed by at least one of the one or more processors, cause the computing system to perform operations, the operations comprising:
generating a measured pressure response curve based at least partially upon a pressure response that is measured by a sensor in a wellbore, wherein the pressure response is generated by firing said perforating gun in the wellbore;
determining one or more functions that approximate the measured pressure response curve;
generating an approximate curve based at least partially upon the one or more functions.

17. The downhole tool of claim 16, wherein the measured pressure response curve, the one or more functions, the approximate curve, or a combination thereof is transmitted from the wellbore to a surface location by said transmitter.

18. The downhole tool of claim 16, wherein the operations further comprise determining an error between the measured pressure response and the one or more functions.

19. The downhole tool of claim 16, wherein the operations further comprise determining an error between the measured pressure response curve and the approximate curve.

20. The downhole tool of claim 16, wherein the operations further comprise dividing the measured pressure response curve into a plurality of segments, wherein each of the one or more functions corresponds to one of the plurality of segments.

* * * * *